United States Patent [19]

Buehler

[11] Patent Number: 5,032,371
[45] Date of Patent: Jul. 16, 1991

[54] PROCESS FOR THE CONTINUOUS RECOVERY OF HYDROGEN FLUORIDE GAS

[75] Inventor: Henry J. Buehler, Affton, Mo.

[73] Assignee: Mallinckrodt Specialty Chemicals Co., St. Louis, Mo.

[21] Appl. No.: 376,572

[22] Filed: Jul. 7, 1989

Related U.S. Application Data

[63] Continuation-in-part of Ser. No. 315,503, Feb. 27, 1989, abandoned.

[51] Int. Cl.⁵ .............................................. C01B 7/19
[52] U.S. Cl. ..................................... 423/484; 423/488
[58] Field of Search ......................... 423/484, 483, 488

[56] References Cited

U.S. PATENT DOCUMENTS 2,939,766  6/1960  Churchill .......................... 423/483
4,120,939  10/1978  Ehlig ................................ 423/483

FOREIGN PATENT DOCUMENTS 0214068  6/1985  European Pat. Off. .
2543965  10/1975  Fed. Rep. of Germany ...... 423/484

Primary Examiner—Michael L. Lewis
Assistant Examiner—Brian M. Bolam
Attorney, Agent, or Firm—Rothwell, Figg, Ernst & Kurz

[57] ABSTRACT

A continuous process for the recovery of anhydrous hydrogen fluoride gas by contacting an aqueous solution of an alkali metal fluoride in hydrofluoric acid with a sulfur-containing dehydrating stream. The dehydrating stream preferably consists of sulfur trioxide dissolved in sulfuric acid. The desired product is obtained in high yield and purity.

9 Claims, 1 Drawing Sheet

PROCESS FOR THE CONTINUOUS RECOVERY OF HYDROGEN FLUORIDE GAS

This application is a continuation-in-part of U.S. Pat. application Ser. No. 315,503, filed Feb. 27, 1989, now abandoned.

FIELD OF THE INVENTION

The present invention relates to the recovery of hydrogen fluoride gas and, more particularly, to the continuous recovery of hydrogen fluoride as an anhydrous gas by contacting an aqueous solution of an alkali metal fluoride in hydrofluoric acid with a dehydrating sulfur-containing stream. The invention is well suited to be integrated with another process, e.g. one which generates large quantities of aqueous hydrogen fluoride.

BACKGROUND OF THE INVENTION

A number of physical and chemical methods have, in the past, been utilized to generate or recover anhydrous hydrogen fluoride gas from various aqueous hydrofluoric acid solutions. The existing methods suffer many disadvantages including low yield and low purity of the desired final product, high complexity in the design and operation of the process apparatus and difficulty in the disposal and/or neutralization of the waste or residue from which the hydrogen fluoride gas evolves. Many of the existing methods for the recovery of hydrogen fluoride are suitable only for batch mode processing which, in and of itself, has disadvantages when compared to the preferred continuous process mode.

The recovery of anhydrous hydrogen fluoride gas from aqueous solutions often is carried out as a step necessary to render economical some other process which results in the generation of large quantities of impure hydrofluoric acid. For example, U.S. Pat. No. 2,939,766 (Churchill, June 7, 1960) relates to the recovery of hydrogen fluoride from a mixture which consists essentially of an alkali metal bifluoride and hydrogen fluoride - water azeotrope. The mixture results during the preparation of fluorobenzene by the diazotization of aniline and subsequent decomposition of the benzenediazonium fluoride in the presence of excess hydrogen fluoride. In the Churchill process, which is carried out in the batch mode, the above described mixture is cooled to 0° C., admixed with sulfur trioxide and then heated to distill off hydrogen fluoride. The process is a batch process, however, uses a relatively large amount of sulfur trioxide and is relatively energy intensive. The large quantity of sulfur trioxide may lead to contamination of the final hydrogen fluoride product, and the initial cooling step requires excess time and energy.

U.S. Pat. No. 4,120,939 (Ehlig, Oct. 17, 1978) discloses a continuous process for the production of hydrogen fluoride by dropping small particles of a metal fluoride, such as calcium fluoride (fluorspar), through a reaction zone countercurrent to a gas stream containing sulfur trioxide, sulfuric acid and water vapor which is introduced at the bottom of the reactor zone. Optionally, hydrogen fluoride or another gas inert to the reaction (such as air) also is introduced at the bottom of the reactor zone.

SUMMARY OF THE INVENTION

In accordance with the present invention there is provided a process for the continuous production of substantially anhydrous hydrogen fluoride gas which comprises contacting an aqueous stream of alkali metal fluoride-containing hydrofluoric acid with a dehydrating sulfur-containing stream, thereby forming a mixed stream; introducing the mixed stream into an upper portion of a heat recovery tower whereby hydrogen fluoride gas evolves from the mixed stream; passing the mixed stream through the heat recovery tower while contacting the mixed stream with a countercurrent flow of heated hydrogen fluoride gas whereby additional hydrogen fluoride gas evolves from the mixed stream; passing the mixed stream from the heat recovery tower to a high temperature reactor vessel; and heating the mixed stream in the vessel to further evolve hydrogen fluoride gas from the mixed stream.

The hydrofluoric acid solution can, but need not, originate as a by-product of another chemical process. For example, the present process finds utility in the recovery of hydrogen fluoride from the heel which results during the preparation of aromatic fluorides according to the process disclosed in our copending application Ser. No. 124,501 filed Nov. 24, 1987 and now U.S. Pat. No. 4,822,927. Those skilled in the art will readily adapt the present process for use with other sources of hydrofluoric acid.

The process of the invention advantageously is operated in the continuous mode, making it particularly attractive for utilization downstream of another continuous process, i.e., one which generates aqueous hydrogen fluoride as a by-product. The process incorporates the use of a heat recovery (heat exchanger) tower which helps to minimize the heating and cooling requirements of this recovery process which, therefor, is less energy intense and is safer than prior art batch processes. This requirement for less energy input also results in a less corrosive environment within the reactor equipment. The process further provides a final product exhibiting high purity and a waste stream which is easily handled. The waste stream is essentially a fluid rather than a semi-solid sludge, especially when the sulfur-containing dehydrating stream includes sulfuric acid. Thus, the waste stream flows from the vessel as opposed to requiring mechanical means to remove it.

DETAILED DESCRIPTION OF THE INVENTION

Figure 1:
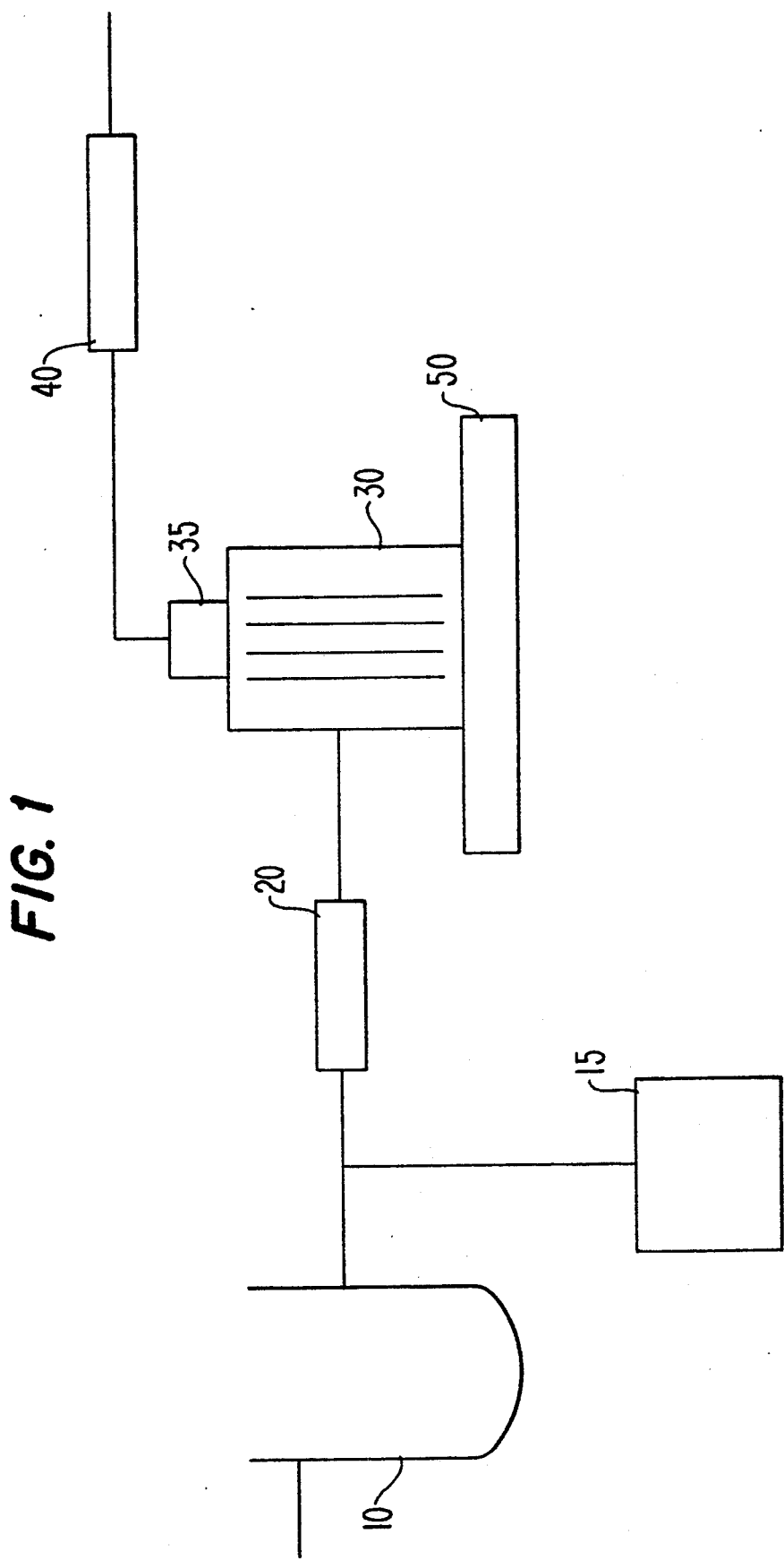
FIG. 1 is a schematic illustration of the process of the invention in which anhydrous hydrogen fluoride gas is recovered from a solution of an alkali metal fluoride in hydrofluoric acid.

Aqueous hydrogen fluoride (hydrofluoric acid), one of the starting materials for the process of the invention, may be prepared or otherwise obtained via any suitable method. For the purposes of this description, however, a preferred embodiment of the present process will be described in connection with the utilization of the hydrogen fluoride-containing aqueous heel which remains after the decomposition of aromatic diazonium fluorides during the preparation of aromatic fluorides according to the process of the above-mentioned application, now U.S. Pat. No. 4,822,927. This heel nominally contains about 80 percent by weight hydrogen fluoride, about 9 percent by weight water, about 10 percent by weight alkali metal fluoride and about 1 percent by weight of organic impurities. The organic impurities are carry over diazonium salt-decomposition product, by-products of the diazotization reaction and by-products of the decomposition reaction.

As a first step in the process of this invention, the aqueous heel is pumped via inlet line 5 into holding tank 10. Although it is contemplated that the heel will most often be a by-product of another process, the invention is not so limited. The heel is received into the holding tank at a temperature above 0° C. This 0° C. temperature limitation is desired to avoid the possibility of the alkali metal fluoride precipitating out of solution. The heel is then maintained within holding tank (10) at a temperature between 0 and 40° C., preferably between 25 and 40° C. and most preferably between 35 and 40° C.

Although the process is not so limited, sodium fluoride is the particular alkali metal fluoride contained in the heel from the diazotization-decomposition process. Aqueous heels containing potassium fluoride also would be useful in the process. The concentration of alkali metal fluoride in the solution is not critical and the present process can tolerate wide variations. The heel resulting from the diazotization-decomposition process, for example, contains from about 9 to 10.5 percent by weight of alkali metal fluoride, and more usually 10.1 to 10.5 percent.

Anhydrous hydrogen fluoride is recovered from the alkali metal fluoride-containing heel during subsequent process steps which conveniently are carried out in the continuous mode. The alkali metal-containing heel is pumped from the holding tank in a continuous stream which as a first step is contacted and intimately mixed with a sulfur-containing dehydrating stream (to form a "mixed stream") in a static mixing apparatus (20). The dehydrating stream is stored within reservoir 15 and preferably consists of sulfur trioxide dissolved in sulfuric acid. The dehydrating stream can contain from 20 to 90 percent sulfur trioxide in sulfuric acid, preferably 65 to 80 percent and most preferably 65 percent. By percent it is meant parts of sulfur trioxide to parts of 100% $H_2SO_4$. A dehydrating stream consisting entirely of sulfur trioxide or sulfuric acid also is useful. Preferably, the sulfur-containing stream will be combined with the heel so as to provide a ratio of 0.8 to 0.9, and more preferably 0.81 to 0.84, moles of $SO_3$ per mole of water. The volume of the stream can then vary with the strength of the oleum (% $SO_3$ in $H_2SO_4$) and the percent water in the heel to be treated.

The use of sulfuric acid is quite advantageous as many of the possible contaminants and impurities remain dissolved in the sulfuric acid throughout the process, lending itself to a continuous mode of neutralization upon removal. The sulfuric acid also contributes to the fluidity of the waste but requires neutralization with caustic. Thus, the respective properties of sulfur trioxide and sulfuric acid are balanced by utilizing a mixture of the two.

The mixed steam is pumped into the top of a heat recovery tower (30) to begin the separation phase of the process. At this point a portion (nominally about fifteen percent) of the total hydrogen fluoride content of the mixed stream evolves as a gas and is separated from the remainder of the mixed stream. The hydrogen fluoride gas is admitted into a distillation tower (35) for the removal of small amounts of water and/or $SO_3$ vapor that may escape along with the hydrogen fluoride gas. Any water vapor and/or $SO_3$ so removed flow back into the heat recovery tower (30) while the hydrogen fluoride gas is admitted into condenser (40). While the use of a distillation tower (35) is not essential to the present process, it is desired due to its positive impact on the purity of the recovered hydrogen fluoride.

Substantially anhydrous hydrogen fluoride is condensed within the condenser (40). The remaining portion of the mixed stream cascades down through the heat recovery tower (30) while high temperature (100 to 190° C., preferably 125 to 155° C.) hydrogen fluoride vapor is passed upwards through the tower. The falling mixed stream and rising hydrogen fluoride vapor reach thermal equilibrium within the tower whereupon additional hydrogen fluoride gas (nominally about fifty to sixty percent of the original hydrogen fluoride content of the mixed stream) evaporates. The hydrogen fluoride gas rises through the heat recovery tower and is separated along with the initial hydrogen fluoride portion for transport to the condenser (40).

The remaining mixed stream, with the majority of the hydrogen fluoride removed, exits the tower and is drained into a continuously underflowing high temperature reactor (50). The residence time within this reactor is adjusted so that the residual hydrogen fluoride can be distilled off and the alkali metal bifluoride can be converted to two moles of hydrogen fluoride and subsequently recovered. A residence time of from 60 to 180 minutes, preferably 100 to 135 minutes, should be sufficient. Advantageously the hydrogen fluoride gas separated within the high temperature reactor (50) is utilized as the countercurrent, high temperature hydrogen fluoride gas stream within the heat recovery tower. The efficiency of the process is enhanced by supplying heat recovered from within the tower (30) to the underflowing reactor vessel (50).

The remaining waste is of the nature of a homogeneous sulfuric acid solution with low viscosity at process temperatures. This permits the recovery process to run continuously because the waste can easily underflow out of the reactor and be continuously neutralized. This also allows total automation of the present process through to waste discharge and neutralization. As mentioned above, sulfuric acid provides fluidity to the waste leading to the advantages of easier mixing for neutralization and better heat transfer in the high temperature reactor. This permits the use of less complicated and less expensive equipment (for example, a physical stirrer is not required). Better heat transfer occurs, which translates into lower heat input into the system, less corrosion and thus longer equipment life.

The following Example is intended to illustrate the practice of the present process without in any way limiting the scope of protection sought.

EXAMPLE

A hydrogen fluoride-containing aqueous heel by-product from the diazotization reaction of U.S. Pat. No. 4,822,927 was used as the source of aqueous hydrogen fluoride for use in the process of the present invention. The heel was analyzed and found to contain, by weight, 79.5% HF, 9.1% water, 10.6% NaF and 0.8% organics. The solution was pumped through a static mixer where the solution stream was contacted and intimately mixed with a dehydrating stream of 65% oleum (65% by weight $SO_3$ dissolved in 100% $H_2SO_4$) to provide a ratio of 0.83 moles $SO_3$ per mole of water in the heel. The resulting mixed stream was admitted into the top of the heat recovery tower where a portion of the hydrogen fluoride gas immediately flashed off. The hydrogen fluoride gas was captured and passed through a one pass shell and tube heat exchanger whereby substantially pure, anhydrous hydrogen fluoride gas was obtained. The remaining mixed stream cascaded down through the plates of the heat recovery tower and was contacted therein by a rising hydrogen fluoride gas stream which had been heated to a temperature of approximately 125 to 155° C. The mixed stream and rising vapors reached thermal equilibrium at about 50 to 55° C. within the tower, whereupon a large volume of hydrogen fluoride gas evaporated from the mixed stream. This portion of hydrogen fluoride gas rose through the tower and was collected at the top and admitted to the condenser. The remaining mixed stream entered a high temperature reactor composed of corrosion-resistant steel alloy with internal heating coils installed as a continuously underflowing reactor immediately beneath the heat recovery tower. This reactor, operating at approximately 125 to 155° C., converted the residual sodium bifluoride to hydrogen fluoride gas. Residence time in this reactor was approximately 100 to 135 minutes.

Although the present process has been described in connection with certain preferred embodiments, it is not so limited. Modifications within the scope of the appended claims will be readily apparent to those skilled in the art.

I claim:

1. A process for the continuous recovery of hydrogen fluiride gas from an aqueous hydrofluoric acid solution containing alkali metal fluoride which comprises:

contacting an aqueous stream of alkali metal fluoride-containing hydrofluoric acid with a sulfur-containing dehydrating stream which comprises from about 20 to about 90 percent sulfur trioxide in sulfuric acid, thereby forming a mixed stream;

introducing the mixed stream into an upper portion of a heat recovery tower whereby hydrogen fluoride gas evolves from the mixed stream;

passing the mixed stream through the heat recovery toward while contacting the mixed stream with a countercurrent flow of heated hydrogen fluoride gas whereby additional hydrogen fluoride gas evolves for the mixed stream;

passing the mixed stream for the heat recover toward to a reactor vessel; and heating the mixed stream in the reactor vessel to further evolve hydrogen fluoride gas from the mixed stream.

2. A process in accordance with claim 1 wherein hydrogen fluoride gas which evolves for the mixed stream is transported through a distillation tower.

3. A process in accordance with claim 1 wherein said dehydrating stream comprises sulfuric acid.

4. A process in accordance with claim 1 wherein said dehydrating stream comprises from about 65 to about 80 percent sulfur trioxide in sulfuric acid.

5. A process in accordance with claim 1 wherein said dehydrating steam comprises about 65 percent sulfur trioxide in sulfuric acid.

6. A process in accordance with claim 1 wherein said alkali metal fluoride is selected from the group consisting of sodium fluoride and potassium fluoride.

7. A process in accordance with claim 1 wherein said contacting step comprises contacting said aqueous stream with an amount of said dehydrating stream corresponding to about 0.8 to 0.9 moles of sulfur trioxide in said dehydrating stream per mole of water in said aqueous stream.

8. A process in accordance with claim 1 wherein said contacting step comprises contacting said aqueous stream with an amount of said dehydrating stream corresponding to about 0.81 to 0.84 moles of sulfur trioxide i said dehydrating stream per mole of water in said aqueous stream.

9. A process in accordance with claim 1 wherein said contacting step comprises contacting said aqueous stream with an amount of said dehydrating steam corresponding to about 0.83 moles of sulfur trioxide in said dehydrating stream per mole of water in said aqueous stream.

* * * * *